United States Patent [19]  [11]  4,410,538
Hamprecht et al.  [45]  Oct. 18, 1983

[54] N-DISUBSTITUTED ANILINE DERIVATIVES, THEIR PREPARATION, THEIR USE AS MICROBICIDES AND AGENTS FOR SUCH USE

[75] Inventors: Gerhard Hamprecht, Weinheim; Eberhard Ammermann, Ludwigshafen; Ernst-Heinrich Pommer, Limburgerhof; Peter Plath, Ludwigshafen, all of Fed. Rep. of Germany

[73] Assignee: BASF Aktiengesellschaft, Fed. Rep. of Germany

[21] Appl. No.: 287,684

[22] Filed: Jul. 28, 1981

[30] Foreign Application Priority Data

Aug. 14, 1980 [DE] Fed. Rep. of Germany ....... 3030736

[51] Int. Cl.³ .................... C07D 285/06; A01N 43/82
[52] U.S. Cl. ..................................... 424/270; 548/127
[58] Field of Search ......................... 548/127; 424/270

[56] References Cited

U.S. PATENT DOCUMENTS 4,177,054 12/1979 Arndt et al. ......................... 548/127
4,314,839 2/1982 Krüger et al. ...................... 548/127

FOREIGN PATENT DOCUMENTS 10163 4/1980 European Pat. Off. .
19742 11/1980 European Pat. Off. .
2513732 10/1975 Fed. Rep. of Germany .
2513788 10/1975 Fed. Rep. of Germany .
2728523 6/1977 Fed. Rep. of Germany .
2909991 10/1980 Fed. Rep. of Germany .
2045757A 11/1980 United Kingdom .

Primary Examiner—Mary C. Lee
Attorney, Agent, or Firm—Keil & Witherspoon

[57] ABSTRACT

N-Disubstituted aniline derivatives of the formula

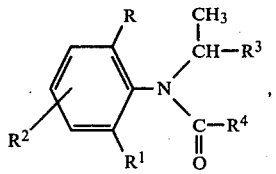

where R is $C_1$–$C_4$-alkyl, $C_1$–$C_4$-alkoxy, $C_2$–$C_4$-alkoxyalkyl or halogen, $R^1$ is $C_1$–$C_4$-alkyl or halogen, $R^2$ is hydrogen, $C_1$–$C_4$-alkyl or halogen, $R^3$ is $CH[OR^5]_2$, $COOR^5$ or $COSR^5$, $R^5$ being $C_1$–$C_4$-alkyl, and $R^4$ is unsubstituted or methyl-, nitro- or halogen-substituted 1,2,3-thiadiazol-4-yl or 1,2,3-thiadiazol-5-yl, and the manufacture thereof.

The novel compounds have microbicidal properties.

7 Claims, No Drawings

N-DISUBSTITUTED ANILINE DERIVATIVES, THEIR PREPARATION, THEIR USE AS MICROBICIDES AND AGENTS FOR SUCH USE

The present invention relates to novel N-disubstituted aniline derivatives, processes for their preparation, microbicides which contain these compounds as active ingredients, and processes for control of fungi.

Heterocyclic carboxylic acid anilides which have a microbicidal action are disclosed in German Laid-Open Applications DOS No. 2,513,732 and DOS No. 2,513,788. Heterocyclic radicals in these compounds are pyridyl, pyrimidinyl, dihydropyranyl, dihydro-1,4-oxathiinyl, thienyl and furyl. These compounds are insufficiently active against Phytophthora.

We have found that N-disubstituted aniline derivatives of the formula I

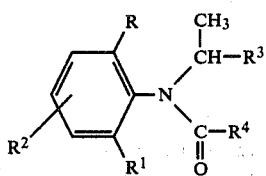

where R is $C_1$–$C_4$-alkyl, $C_1$–$C_4$-alkoxy, $C_2$–$C_4$-alkoxyalkyl or halogen, $R^1$ is $C_1$–$C_4$-alkyl or halogen, $R^2$ is hydrogen, $C_1$–$C_4$-alkyl or halogen, $R^3$ is $CH[OR^5]_2$, $COOR^5$ or $COSR^5$, $R^5$ being $C_1$–$C_4$-alkyl, and $R^4$ is unsubstituted or methyl-, nitro- or halogen-substituted 1,2,3-thiadiazol-4-yl or 1,2,3-thiadiazol-5-yl, possess excellent microbicidal activity and are superior to known heterocyclic carboxylic acid anilides in their action, especially against Phytophthora.

Preferred microbicides are compounds of the formula I, where R, $R^1$ and $R^2$ independently of one another are methyl, ethyl, n-propyl, i-propyl, n-butyl, i-butyl, sec.-butyl, tert.-butyl, fluorine, chlorine, bromine or iodine, R can also be methoxymethyl, ethoxymethyl, methoxyethyl, ethoxyethyl, methoxy, ethoxy or n-propoxy, $R^2$ can also be hydrogen, $R^3$ can also be dimethoxymethyl, carbomethoxy or carbomethylmercapto and $R^4$ has the stated meanings.

Particularly preferred compound of the formula I are those where R is methyl, $R^1$ is methyl, ethyl or chlorine, $R^2$ is hydrogen or methyl, $R^3$ is dimethoxymethyl, carbomethoxy or carbomethylmercapto and $R^4$ is 1,2,3-thiadiazol-4-yl or 1,2,3-thiadiazol-5-yl.

The compounds of the formula I can be prepared by reacting a compound of the formula II

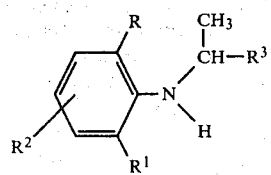

where R, $R^1$, $R^2$ and $R^3$ have the above meanings, with a carboxylic acid derivative of the formula III

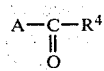

where $R^4$ has the above meanings and A is a nucleophilically displaceable leaving group.

In formula III, A is, for example, halogen, eg. chlorine or bromine, alkoxycarbonyloxy, eg. methoxycarbonyloxy or ethoxycarbonyloxy, benzyloxycarbonyloxy or an azolyl radical, eg. imidazolyl or triazolyl.

Though the reaction can also be carried out in the absence of a solvent, it is advantageous to employ an inert solvent or diluent. Examples of suitable solvents are halohydrocarbons, especially chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, m- and p-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, eg. nitromethane, nitroethane, nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone and methyl ethyl ketone; and, where appropriate, also water, and mixtures of the above. Advantageously, the amount of solvent used is from 100 to 2,000% by weight, preferably from 200 to 700% by weight, based on starting material II.

It is advantageous, though not essential, to carry out the reaction in the presence of an acid acceptor. All conventional acid-binding agents can be used for this purpose. Preferred examples are tertiary amines, alkaline earth metal compounds, ammonium compounds and alkali metal compounds, as well as mixtures of these. However, zinc compounds can also be used. Specific examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methyl-pyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

However, the hydrogen halide formed in the reaction can also be removed by passing an inert gas, for example nitrogen, into the mixture.

The reaction can be carried out in the presence or absence of an accelerator. Preferred accelerators include metal halides, eg. sodium bromide and potassium iodide, azoles, eg. imidazole and 1,2,4-triazole, pyridines, eg. 4-dimethylaminopyridine, and amides, eg. dimethylformamide, as well as mixtures of these compounds. Advantageously, from 0.9 to 1.3 moles of acid derivative of the formula III, with or without from 0.5 to 1.5 moles of base and with or without from 0.01 to 0.1 mole of reaction accelerator are employed per mole of aniline derivative of the formula II.

The process for the preparation of the novel compounds is advantageously carried out by taking the starting material II, with or without one of the above diluents, and then adding the starting material III and an acid acceptor simultaneously or successively. It is however also possible to introduce the starting material III into one of the above diluents and then to add the starting material II and an acid acceptor, simultaneously or in optional sequence from two separate feeds.

The reaction is in many cases complete as soon as the components have been brought together; if not, the mixture is stirred for from 10 minutes to 10 hours at from −10° to 120° C., preferably from 0° to 100° C., especially from 20° to 80° C.

The compound I is isolated from the reaction mixture in a conventional manner, for example by distilling off the solvent or excess starting material II or III, or directly by filtration. In the latter case, the filter residue is washed with water or dilute alkali or acid to remove acidic or basic impurities, and is then dried. Where a water-immiscible diluent is used, it is also possible to extract the reaction mixture directly with water or dilute alkali or acid, and then to dry it and evaporate it down. It is however also possible to dissolve the residue in a water-immiscible solvent and wash the solution as described. The desired end products are thereby obtained in a pure form; if not, they can be purified further by recrystallization, chromatography or distillation.

The compounds II can be obtained by reacting the corresponding aniline derivative with a compound of the formula IV

Hal—CH(CH₃)—R³        IV where Hal is halogen, for example chlorine or bromine. Details of the preparation of the starting materials of the formula II may be found in the description of the general methods of preparation of anilino-alkanoic acid esters in J. Org. Chem. 30 (1965), 4101, Tetrahedron 1967, 487 and Tetrahedron 1967, 493.

The carboxylic acid derivatives of the formula III used as starting materials are known or can be prepared by known methods, cf. J. Amer. Chem. Soc. 77 (1955), 5359 and J. Chem. Soc. 1965, 5166.

The compounds I have an asymmetric carbon atom in the propionate side chain. They can be separated into the optical antipodes by conventional methods; the D-enantiomer has the more powerful microbicidal action.

Accordingly, within the scope of the present invention, those compounds which have the D-configuration of the formula I, agents containing these compounds, and their use, are preferred.

To prepare the pure optical D-antipodes, it is possible, for example, to react aniline with an α-halopropionic acid to give the racemic compound of the formula V

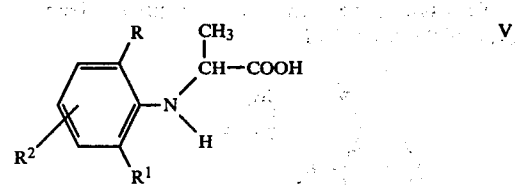

where R, R¹ and R² have the above meanings, and then to convert this to the corresponding salt with an N-containing optically active base, in a conventional manner. Fractional crystallization of the salt and subsequent liberation of the acid V, enriched in the optical D-antipode, followed, if necessary, by one or more repetitions of the sequence of salt formation, crystallization and liberation of the α-anilinopropionic acid V, leads stepwise to the pure D-form. From this the optically active ester II can be prepared in a conventional manner, for example by reacting methylmercaptan or methanol or, preferably, their salts, especially their Na or K salts, with an acid halide of the optical antipode of the formula V. The ester II is then reacted with III in accordance with the invention.

A suitable optically active organic base is, for example, α-phenylethylamine.

Independently of the optical isomerism, an atropic isomerism (=molecular dissymetry due to restricted rotation) about the phenyl—N<axis is as a rule observed in cases where the phenyl ring is substituted unsymmetrically to this axis (which situation can also arise through the presence of additional substituents).

Unless the synthesis is deliberately such as to lead to the isolation of a pure isomer, the product obtained is normally a mixture of two optical isomers or two atropic isomers or a mixture of these four possible isomers. However, the fundamentally better fungicidal action of the enantiomeric D-form (as compared to the D,L-form or to the L-form) still applies and is not significantly influenced by the atropic isomerism.

The Examples which follow illustrate the invention, without restricting its scope. Unless stated otherwise, any reference to an active compound of the formula I, which can exist in optically active forms, is to be taken to mean the racemic mixture.

EXAMPLE 1

53.6 parts of 2,6-dimethylpyridine and 74.3 parts of 1,2,3-thiadiazole-4-carboxylic acid chloride were introduced in parallel, from two feeds, into a stirred solution of 103.7 parts of N-(1'-methoxy-carbonylethyl)-2,6-dimethyl-aniline in 350 parts of methylene chloride at 20°-25° C. The reaction mixture was stirred for 1 hour at 25° C. and the hydrochloride precipitated was filtered off. The filtrate was washed with a small amount of saturated sodium carbonate solution and then three times with N hydrochloric acid, dried over magnesium sulfate and filtered. The solvent was stripped off under reduced pressure and the residue was triturated with a 1:3 mixture of methyl tert.-butyl ether and petroleum ether and filtered off. After drying, the colorless crystals of N-(1'-methoxy-carbonylethyl)-N-(1",2",3"-thiadiazole-4"-carbonyl)-2,6-dimethyl-aniline melted at 86°-90° C.

EXAMPLE 2

21 Parts of N-(1'-methoxy-carbonyl-ethyl)-2-methyl-6-ethyl-aniline and 9.6 parts of triethylamine were introduced in parallel, from two feeds, into a stirred solution of 12.6 parts of 1,2,3-thiadiazole-4-carboxylic acid chloride in 100 parts of ethyl acetate at from −10° to 0° C. The reaction mixture was then stirred for 1 hour at 20° C., and washed three times with N hydrochloric acid and with water. It was then dried, chromatographed over neutral alumina and evaporated down under reduced pressure to give N-(1'-methoxycarbonyl-ethyl)-N-(1",2",3"-thiadiazole-4"-carbonyl)-2-methyl-6-ethylaniline as a pale yellowish oil, $n_D^{25} = 1.5653$.

EXAMPLE 3

12.6 Parts of 1,2,3-thiadiazole-4-carboxylic acid chloride were added, in the course of 10 minutes, to a stirred mixture of 19 parts of N-(1'-dimethoxy-propyl-2'(-2,6-dimethylaniline and 10.3 parts of N,N-dimethylaniline in 130 parts of toluene at 30° C. The reaction mixture was then stirred for 30 minutes at 30° C., and thereafter washed with a small amount of saturated sodium carbonate solution and then three times with N hydrochloric acid. It was then dried and evaporated down under reduced pressure, giving N-(1'-dimethoxypropyl-2')-N-(1",2",3"-thiadiazole-4"-carbonyl)-2,6-dimethylaniline as a pale yellowish oil, $n_D^{25} = 1.5710$.

EXAMPLE 4

14.1 parts of 1,2,3-thiadiazole-4-carboxylic acid chloride and 8.5 parts of pyridine were added in parallel, from 2 feeds, in the course of 10 minutes to a stirred mixture of 19.6 parts of N-(1'-methoxy-carbonylethyl)-2-methyl-6-chloroaniline and 100 parts of 1,2-dichloroethane at 20°-35° C. After 30 minutes' stirring at 60° C., the reaction mixture was washed with saturated sodium carbonate solution and then three times with N hydrochloric acid, dried, chromatographed over alumina and evaporated down under reduced pressure, to give N-(1'-methoxy-carbonyl-ethyl)-N-(1",2",3"-thiadiazole-4"-carbonyl)-2-methyl-6-chloroaniline as colorless crystals of melting point 59°-62° C.

The following compounds of the formula I can be prepared similarly to Example 1:

| No. | R | $R^1$ | $R^2$ | $R^3$ | $R^4$ | m.p. °C./$n_D^{25}$ |
|---|---|---|---|---|---|---|
| 5 | $CH_3$ | $CH_3$ | 4-Cl | $CO_2CH_3$ | thiadiazole | |
| 6 | $CH_3$ | $CH_3$ | H | $CO_2CH_3$ | thiadiazole | |
| 7 | $CH_3$ | Cl | H | $CO_2CH_3$ | thiadiazole | |
| 8 | $CH_3$ | $CH_3$ | H | $CH(OCH_3)_2$ | thiadiazole | |
| 9 | $CH_3$ | $CH_3$ | 3-$CH_3$ | $CO_2CH_3$ | thiadiazole | 1.5610 |
| 10 | $CH_3$ | Cl | H | $CO_2CH_3$ | $CH_3$-thiadiazole | |
| 11 | $CH_3$ | $CH_3$ | H | $CO_2CH_3$ | Cl-thiadiazole | |
| 12 | $OCH_3$ | $CH_3$ | H | $CO_2CH_3$ | $CH_3$-thiadiazole | |

-continued

| No. | R | R¹ | R² | R³ | R⁴ | m.p. °C./$n_D^{25}$ |
|---|---|---|---|---|---|---|
| 13 | CH₃ | CH₃ | H | COSCH₃ | (thiadiazole ring) | |
| 14 | CH₃ | CH₃ | H | CO₂CH₃ | CH₃-substituted thiadiazole | |
| 15 | CH₃ | CH₃ | H | CO₂CH₃ | CH₃-substituted thiadiazole | 124 |

The active ingredients according to the invention have a strong fungitoxic action. They cause no damage to crop plants in the concentrations necessary for combating fungi and bacteria. For these reasons they are suitable for use as crop protection agents for fighting fungi.

The new active ingredients exhibit a strong fungitoxic action on phytopathogenic fungi. They are suitable for combating for instance *Erysiphe graminis* in cereals, *Erysiphe cichoriacearum* in Cucurbitaceae, *Erysiphe polygoni* in beans, *Podosphaera leucotricha* and *Phytophthora cactorum* in apples, *Phytophthora infestans* in tomatoes and potatoes, *Phytophthora parasitica* in strawberries, *Pseudoperonospora cubensis* in cucumbers, *Pseudoperonospora humuli* in hops, *Peronospora destructor* in onions, *Peronospora tabacina* in tobacco, *Peronospora sparsa* in roses, *Plasmopara viticola* in grapes, *Plasmopara halstedii* in sunflowers, *Sclerospora macrospora* in Indian corn, *Bremia lactucae* in lettuce, *Mucor mucedo* in fruit, *Rhizopus nigricans* in beets, *Uncinula necator* in grapes, and *Sphaerotheca pannosa* in roses.

The application rates depend on the type of effect desired, and range from 0.1 to 5 kg of active ingredient per hectare. Some of the active ingredients have curative properties, i.e., the agents may also be applied after the plants have been infected by the pathogen, and success is still ensured. Furthermore, many of the new compounds have a systemic action, which means that visible plant parts may also be protected by a root treatment.

The new compounds may also be employed to control fungi which cause seedling and emergence diseases, e.g., Pythium and Aphanomyces species in Leguminosae and cotton. The agents are applied as seed disinfectants at rates of from 10 to 200 g per 100 kg of seed.

The compounds are applied by spraying or dusting the plants with the active ingredients, or treating the seed with them. The compounds may be applied before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients, because fungicidal effectiveness is favorably influenced the finer the particles are. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt % of active ingredient.

The agents, and the ready-to-use formulations obtained therefrom, e.g., solutions, emulsions, suspensions, powders, dusts, pastes or granules, are applied in the conventional manner, e.g. by spraying, atomizing, dusting, scattering, treating seed, or watering.

Examples of such formulations are given below:

I. 90 Parts by weight of the compound of Example 9 is mixed with 10 parts by weight of N-methyl-α-pyrrolidone. A mixture is obtained which is suitable for application in the form of very fine drops.

II. 20 Parts by weight of the compound of Example 1 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 Parts by weight of the compound of Example 4 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 Parts by weight of the compound of Example 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 Parts by weight of the compound of Example 4 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 Parts by weight of the compound of Example 9 is intimately mixed with 97 parts by weight of particulate kaolin. A dust is obtained containing 3% by weight of the active ingredient.

VII. 30 Parts by weight of the compound of Example 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 Parts by weight of the compound of Example 2 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt % of active ingredient.

IX. 20 Parts of the compound of Example 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The above ready-to-use preparations may contain other active ingredients together with those according to the invention, e.g. herbicides, insecticides, growth regulators and other fungicides or may be mixed with fertilizers and applied together with these. When the active ingredients are mixed with other fungicides, the fungicidal spectrum of action is in many cases broadened.

The list of fungicides given below, with which the compounds according to the invention can be combined, is intended to illustrate the possible combinations, but the invention is in no way limited to these.

Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc, N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc, N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl- 2-dimethylamino-4-hydroxy-6-methyl- -pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclodecyl-morpholine and its salts, diisopropyl 5-nitroisophthalate, 1-(1',2',4'-triazol-1'-yl)-(4'-chlorophenoxy)-3,3-dimethylbutan-2-one, 1-(1',2',4'-triazol-1'-yl)-(4'-chlorophenoxy)-3,3-dimethylbutan-2-ol, N-(n-propyl)-N-(2,4,6-trichlorophenoxyethyl)-N'-imidazolylurea, N-cyclohexyl-N-methoxy-2,5-dimethylfuran-3-carboxylic acid amide, 2,4,5-trimethylfuran-3-carboxylic acid anilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, and N-[3-(p-tert-butylphenyl)-2-methylpropyl]-cis-2,6-dimethylmorpholine.

EXAMPLE A

Fungicidal Action on *Phytophthora infestans* in Tomatoes

Leaves of tomato plants of the "Professor Rudloff" variety are sprayed with aqueous suspensions containing (dry basis) 80% (wt %) of active ingredient and 20% of sodium lignin sulfonate. 0.05 and 0.025% (dry basis) spray liquors are used. After the sprayed-on layer has dried, the leaves are infected with a zoospore suspension of *Phytophthora infestans*. The plants are then placed for 5 days in a steam-saturated (moist) chamber kept at 16° to 18° C. After this period, the disease has spread on the untreated control plants to such an extent that the fungicidal action of the compounds can be assessed.

EXAMPLE B

Fungicidal Action on *Plasmopara viticola* in Grapes

Leaves of potted vines of the Müeller-Thurgau variety are sprayed with aqueous emulsions containing (dry basis) 80% (by weight) of the active ingredient and 20% of emulsifier. 0.025% spray liquors (dry basis) are used. To assess the duration of action of the active ingredients, the plants are placed, after the sprayed-on layer has dried, for 10 days in the greenhouse. The leaves are then infected with a zoospore suspension of Plasmopara viticola. The plants are then placed for 16 hours in a steam-saturated (moist) chamber at 24° C., and subsequently for 8 days in the greenhouse at 20° C. to 30° C. To accelerate and intensify the sporangiophore discharge, the plants are then again placed in the moist chamber for 16 hours. The extent of fungus spread is assessed on the undersides of the leaves.

EXAMPLE C

Action on Wheat Mildew

Leaves of pot-grown wheat seedlings of the "Jubilar" variety are sprayed with aqueous emulsions consisting of 80% (by weight) of active ingredient and 20% of emulsifier, and dusted, after the sprayed-on layer has dried, with spores of wheat mildew (*Erysiphe graminis* var. *tritici*). The plants are then placed in a greenhouse at 20° to 22° C. and 75 to 80% relative humidity. The extent of mildew spread is determined after 10 days.

In Examples A, B, and C, particularly the compounds of Examples 1 to 3 and 9 exhibited much more favorable properties than the prior art active ingredient furalaxyl (D,L-methyl-N-(2,6-dimethylphenyl)-N-fur-2-oyl alanate, German Laid-Open application DE-OS No. 2,513,732).

We claim:

1. An N-disubstituted aniline derivative of the formula

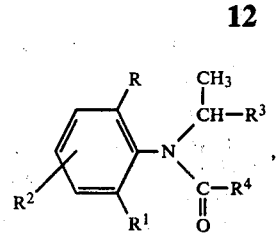

where R is $C_1$–$C_4$-alkyl, $C_1$–$C_4$-alkoxy, $C_2$–$C_4$-alkoxyalkyl or halogen, $R^1$ is $C_1$–$C_4$-alkyl or halogen, $R^2$ is hydrogen, $C_1$–$C_4$-alkyl or halogen, $R^3$ is $CH[OR^5]_2$, $COOR^5$ or $COSR^5$, $R^5$ being $C_1$–$C_4$-alkyl, and $R^4$ is unsubstituted or methyl-, nitro- or halogen-substituted 1,2,3-thiadiazol-4-yl.

2. A compound of the formula I as defined in claim 1, wherein R is methyl, $R^1$ is methyl, ethyl, chlorine or bromine, $R^2$ is hydrogen, m-methyl, m-ethyl or m-chlorine, $R^4$ is 1,2,3-thiadiazol-4-yl and $R^5$ is methyl.

3. A compound of the formula I as defined in claim 1, wherein R is methyl, $R^1$ is methyl or ethyl, $R^2$ is hydrogen, $R^4$ is 1,2,3-thiadiazol-4-yl and $R^3$ is —COOCH$_3$.

4. N-(1'-methoxy-carbonyl-ethyl)-N-(1″, 2″, 3″-thiadiazol-(4″)-carbonyl)-2,6-dimethylaniline.

5. A microbicidal agent comprising at least one N-disubstituted aniline derivative of the formula I as defined in claim 1 and a solid or liquid carrier.

6. A process for combating fungi, wherein at least one N-disubstituted aniline derivative of the formula I as defined in claim 1 is allowed to act on areas, plants or seed threatened by fungus attack.

7. A compound of the formula I as defined in claim 1, wherein $R^1$ is methyl or ethyl, $R^2$ is m-methyl, $R^4$ is 1,2,3-thiadiazol-4-yl and $R^3$ is —COOCH$_3$.